United States Patent [19]
Victor

[11] 4,326,164
[45] Apr. 20, 1982

[54] ELECTRICAL RESISTANCE CORROSION PROBE

[75] Inventor: Joe M. Victor, Houston, Tex.

[73] Assignee: Petrolite Corporation, St. Louis, Mo.

[21] Appl. No.: 130,322

[22] Filed: Mar. 14, 1980

[51] Int. Cl.³ .......................................... G01N 27/00
[52] U.S. Cl. ............................ 324/71 R; 324/65 CR
[58] Field of Search .............. 324/71 E, 71 R, 65 CR

[56] References Cited
U.S. PATENT DOCUMENTS 2,851,570 9/1958 Schaschl.
3,104,355 9/1963 Holmes et al. ..................... 324/71 R
3,286,174 11/1966 Schaschl ......................... 324/65 CR
3,857,094 12/1974 Caldecourt ..................... 324/65 CR Primary Examiner—Michael J. Tokar
Attorney, Agent, or Firm—Sidney B. Ring; Hyman F. Glass

[57] ABSTRACT

An electrical resistance corrosion monitoring probe having a single lateral face of each of two rectangular prismatic elements of similar temperature-resistance characteristics but different thicknesses exposed to the corroding environment. Both the faces are corroded away, but the resistance change is different due to the inverse relationship between resistance and cross-sectional area. A measurement bridge network is used to monitor the change in cross-sectional area of both elements. A preferred probe embodiment, employing resistance elements having equivalent thermal masses and electrical resistances, as by using elements of the same material and of substantially equal lengths and cross-sectional areas, allows the use of a complementary measurement bridge network in its most sensitive region.

20 Claims, 6 Drawing Figures

ELECTRICAL RESISTANCE CORROSION PROBE

BACKGROUND OF THE INVENTION

This invention relates to an apparatus and method for monitoring corrosion occurring in the pipelines and other metallic structures due to a corrosive medium in contact with such structure, and more particularly to an electrical resistance probe for determining corrosion by measuring the change in resistance in electrical resistance elements exposed to such corrosive medium.

U.S. Pat. No. 3,104,355 to Holmes et al discloses, inter alia, an electrical resistance corrosion measuring probe compensated for temperature variations in the corrosive medium by employing two resistance elements of similar material which are both completely exposed to the corrosive medium. One of these elements has a materially larger cross-section than the other so that its resistance changes with corrosion at a measurably different proportional rate than the change occurring in the other element. By connecting the two elements in opposite sides of the galvanometer type measurement bridge circuit, resistance readings may be made. Corrosion of the elements is measured by resistance readings taken either continuously (as by reading resistance variation) or at selected intervals.

The above described probe of Holmes suffers from the disadvantage that one of the exposed resistance elements has a cross-sectional area which is much larger than the other and therefore has a negligible resistance change due to corrosion.

It is an object of this invention to provide an electrical resistance corrosion measuring probe having an excellent thermal response while avoiding the above noted disadvantage of the Holmes et al probe. It is a further object of this invention to provide a probe of this type which allows the use of a complementary measuring bridge circuit in its most sensitive region.

Other objects, features and advantages of the present invention will be apparent from the following description.

SUMMARY OF THE INVENTION

The above and other objects of the invention are achieved by providing a probe for monitoring the corrosion caused by a corrosive medium, the probe comprising a first corrodible resistance element, a second corrodible resistance element having a temperature-resistance characteristic similar to that of the first element, each element being in the shape of a rectangular prism and positioned and adapted to have one lateral face exposed to the corrosive medium, the thickness of the second element being greater than that of the first element. The elements are connected in series by junction means and separate terminal means are connected to each element at its end opposite the junction end. Insulating means encase these elements except for their exposed lateral faces. Conductor means are connected to the junction means and terminal means in a manner to cause the elements to function as adjacent but opposite resistance elements of a measurement bridge circuit and to enable connection of the probe to complementary elements of said bridge circuit external to the probe.

As used in this specification and in the claims, a rectangular prism is to be understood as a prism having a rectangular transverse cross-section. The term "thickness" is to be understood as that dimension of such transverse cross-section which is not exposed to the corrosive medium; and the term "width" as that dimension of such cross-section which is exposed to such medium.

The resistance elements of the probe are formed of material similar in corrodibility to any object to be monitored for corrosion in the corrosive medium, such as the walls of a pipeline in which the probe is mounted.

An additional inventive feature is to employ resistance elements in the probe which have substantially equal thermal masses and resistances, and more particularly, which have substantially equal lengths and cross-sectional areas. It is preferred that these resistance elements be made of the same material.

In the preferred embodiment, the probe includes also support means adapted for flush mounting on pipelines or other structures.

The probe is employed in combination with other elements of a measurement bridge circuit, including two resistance arms in series, at least one of which is variable, a null detector connected between the junction means connecting the resistance elements of the probe and the junction of the two last mentioned resistance arms, and a current source connected between the terminal elements connected to the resistance elements of the probe.

The resistance arms complementing the probe elements may both be variable, or one may be fixed and the other variable. The current source may include signal generating means.

The present invention also includes a method of monitoring the corrosion of a corrodible metal exposed to a corrosive medium, which comprises exposing only the lateral faces of adjacent, electrically opposite resistance elements of a measurement bridge circuit to such medium, and determining the change in potential over a period of time between the junction of these elements and the opposite junction of the bridge while impressing a potential, which may be supplied by a signal generator, across the remaining two junctions of the bridge; the resistance elements with the exposed lateral faces being in the shape of rectangular prisms, the thickness of one of these elements being greater than that of the other. These elements have similar temperature-resistance characteristics and, advantageously, substantially equal resistances and thermal masses, preferably with substantially equal lengths and cross-sectional areas. It is more particularly preferred that these elements be made of the same material.

As indicated above, the resistance arms complementing the probe elements may both be variable or one may be fixed and the other variable.

DESCRIPTION OF THE DRAWINGS

The details of the present invention may be more easily understood by reference to the appended drawing figures, of which.

DESCRIPTION OF THE SPECIFIC EMBODIMENTS

Figure 1:
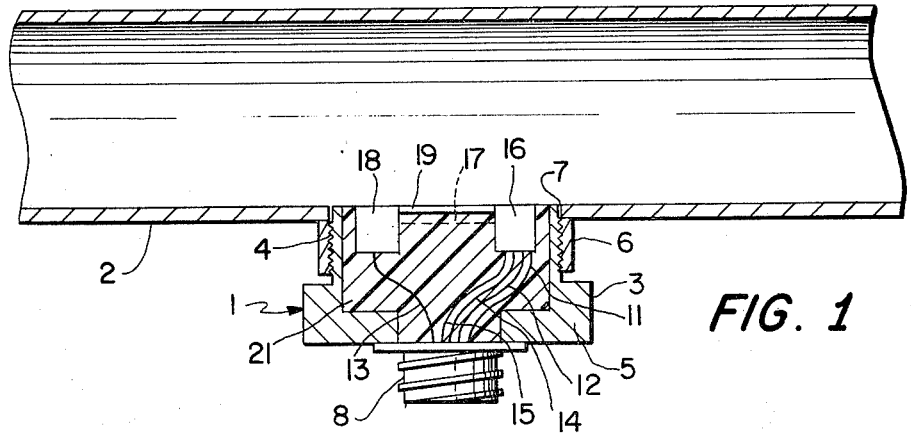
FIG. 1 is a side view, partially in section, at plane 1—1 of FIG. 2, but on a reduced scale with respect to that of FIG. 2, of a pipeline having the corrosion probe of the present invention mounted thereon.

Referring to FIG. 1, an embodiment of a corrosion monitoring probe 1 of the present invention, as adapted for flush mounting in pipelines and other structures containing corrosive fluids, is shown secured to a pipeline 2. The probe 1 includes a probe body 3 consisting of a cylindrical externally threaded portion 4 and an enlarged portion 5 having a polygonal cross-section adapted for engagement with a wrench or the like. In use, the probe 1 is secured to the pipeline 2 by fluid tight (using suitable sealing means) threaded engagement with the interior of a threaded nipple 6, mounted on the pipeline, the axial opening through the nipple being in alignment with a circular opening 7 in the pipeline wall. Further details of such means for flush mounting a probe to a pipeline are described in U.S. Pat. No. 3,996,124 to Eaton et al, which is hereby incorporated by reference. Other suitable means for securing the probe to the pipeline may be substituted. A conventional multipin AN connector 8 is carried exteriorly on the probe body 1.

Figure 2:
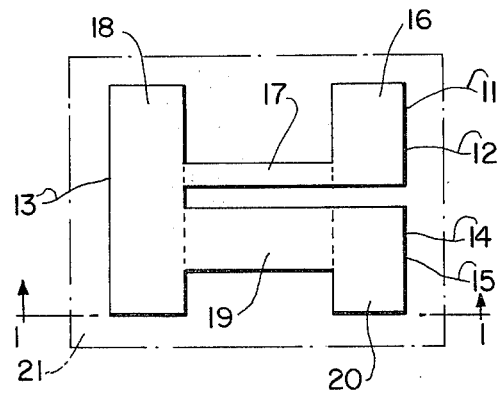
FIG. 2 is a top view of the probe elements as they would appear from inside the pipeline.
Figure 3:
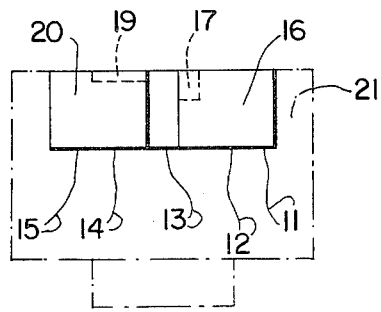
FIG. 3 is an end view of the probe elements.

Referring to FIGS. 2 and 3 as well as FIG. 1, in the interior of the probe body 3 are the electrical components of the probe. These include electrical resistance elements 17 and 19 connected at ends thereof in series by a junction element terminal block 18. Resistance elements 17 and 19 are in the shape of rectangular prisms and are positioned so that when the probe is in place they each have one lateral face exposed to the corroding environment. The resistance elements 17 and 19, as shown, have equal cross-sectional areas and length. However, the thicknesses (and hence the widths) of the resistance elements 17 and 19 are different. The ends of the resistance elements 17 and 19 opposite their junction ends are joined to terminal blocks 16 and 20, respectively. Terminal blocks 16 and 20, as well as junction element terminal block 18, are shown here as rectangular prisms, but other shapes may suitably be employed. A current input lead 11 and a voltage measurement lead 12 are connected to terminal block 16; and a current input lead 15 and a voltage measurement lead 14 are connected to terminal block 20. A lead 13, serving as a voltage bridge common element, is connected to the junction element terminal block 18. Leads 11, 12, 13, 14 and 15 are connected at their ends to connector 8. As shown in the drawing, the electrical components are encased in an insulating material 21, such as an epoxy resin, glass-filled epoxy or ceramic such as glass, with only the upper faces of the resistance elements 17 and 19 and terminal blocks 16, 18 and 20 exposed. If desired, however, the insulating material 21 may cover terminal blocks 16, 18 and 20 entirely. If the upper faces of these terminal blocks are exposed, the blocks should be large enough so that a negligible resistance change occurs if the exposed parts corrode.

Figure 4:
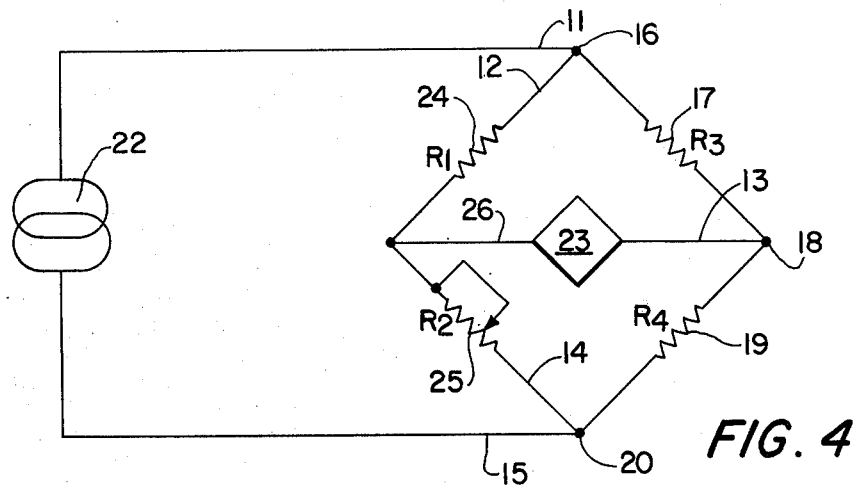
FIG. 4 is a circuit diagram of one embodiment of the measuring apparatus of this invention.

FIG. 4 depicts a measurement bridge circuit including the electrical elements of the above described probe as components. These elements are numbered to correspond with their numbering in FIGS. 1, 2 and 3 and in addition, resistance elements 17 and 19 are designated $R_3$ and $R_4$, respectively, these forming two arms of the measurement bridge. A signal source 22 is connected between current input leads 11 and 15. Constant resistance element 24 and variable resistance element 25, connected in series, and designated also as $R_1$ and $R_2$, respectively, serve as the other two arms of the bridge. Resistance element 24 is connected at its other end to voltage measurement lead 12 and resistance element 25 is connected at its other end to voltage measurement lead 14. A coherent phase null detector 23 is connected between bridge common element 13 and a common element 26 which is connected at its other end to the junction of resistance elements 24 and 25. The signal source 22 is preferably a signal generator which operates at a low (10–200 Hz) A.C. sinusoidal frequency and also provides a synchronous drive to the coherent phase null detector 23.

Figure 5:
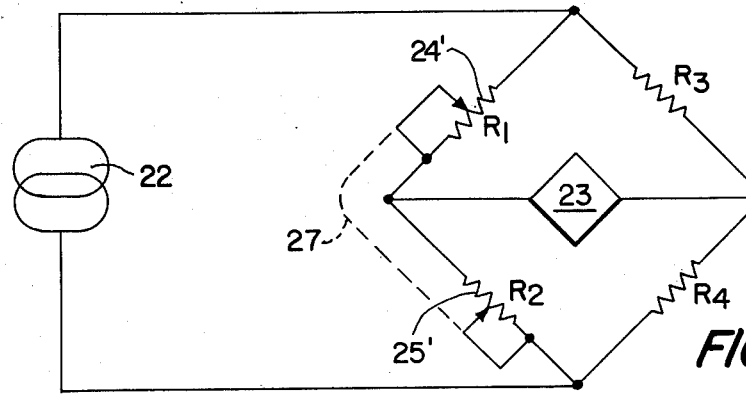
FIG. 5 is a circuit diagram of another embodiment of the measuring apparatus of this invention.

FIG. 5 shows an alternative bridge circuit including the electrical elements of the present probe. Resistance element $R_1$ is here variable resistance 24' and $R_2$ is shown as variable resistance 25'. These variable resistance elements are ganged together, as schematically indicated by dash line 27. Other elements in the circuit are the same as in FIG. 4.

Figure 6:
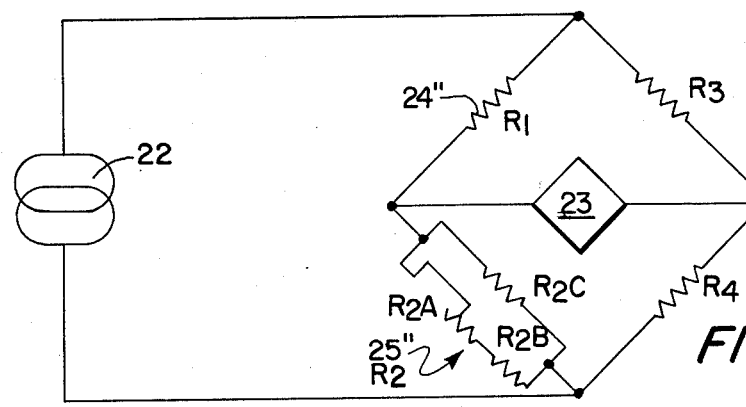
FIG. 6 is a circuit diagram of a further embodiment of the measuring apparatus of this invention.

FIG. 6 shows still another alternative bridge circuit including the electrical elements of the present probe. This is similar to that of FIG. 4, except that resistance $R_2$, shown as 25'', is an equivalent resistance of resistances $R_{2A}$, $R_{2B}$ and $R_{2C}$; $R_{2A}$ being a variable resistance having a maximum value $R_{2AO}$; $R_{2B}$ being a fixed resistance in series with $R_{2A}$; and $R_{2C}$ being a fixed resistance in parallel with the series of $R_{2A}$ and $R_{2B}$.

When the probe of the present invention is used to monitor corrosion, corrosion takes place at the exposed lateral faces of the resistance elements 17 and 19 ($R_3$ and $R_4$, respectively). These elements will both be corroded away but the resistance change will be different due to the inverse relationship between resistance and cross-sectional area.

As indicated above, different thicknesses for the resistance elements in the probe is a necessity. The widths may be the same or different. However, the use of resistance elements having equivalent thermal masses and equivalent resistances allows use of the above described measurement bridges in their most sensitive region, and constitutes an additional inventive feature of the present probe and corrosion measuring apparatus and process.

The principle of the invention, as applied to the above described monitoring circuits, may be more precisely understood by reference to the following mathematical treatment relating particularly to the circuits of FIGS. 5 and 6.

Referring to FIG. 5, the bridge balance condition is:

$$\frac{R_1}{R_2} = \frac{R_3}{R_4}$$

$$R_3 = R_{30} \times F(T) \times \frac{1}{1 - \frac{\Delta t}{t_3}}$$

$$R_4 = R_{40} \times F(T) \times \frac{1}{1 - \frac{\Delta t}{t_4}}$$

Where $R_3$ = resistance of one corroding element
$R_4$ = resistance of second corroding element
$R_{30}$ = resistance of new element 3 at base temperature
$R_{40}$ = resistance of new element 4 at base temperature
$F(T)$ = temperature variation of resistance of corroding elements Δt = change in thickness due to corrosion
$t_3$ = thickness of new 3 element
$t_4$ = thickness of new 4 element
For a balance condition $$\frac{R_1}{R_2} = \frac{R_3}{R_4} = \frac{R_{30} \times F(T) \times \frac{1}{1 - \frac{\Delta t}{t_3}}}{R_{40} \times F(T) \times \frac{1}{1 - \frac{\Delta t}{t_4}}}$$

F(T) drops out of equation as required $$\frac{R_1}{R_2} = \frac{R_{30}\left(1 - \left(\frac{\Delta t}{t_4}\right)\right)}{R_{40}\left(1 - \left(\frac{\Delta t}{t_3}\right)\right)}$$

For simplicity of the bridge design, the potentiometers $R_1$ and $R_2$ are ganged together and selected so that $$R_1 = R_A - XR_B$$

$$R_2 = R_C - XR_D$$

where
$R_A$ = maximum value of variable resistance $R_1$
X = percentage change in resistance $R_B + R_D$
$R_B$ = total resistance change allowable in $R_1$
$R_C$ = maximum value of variable resistance $R_2$
$R_D$ = total resistance change allowable in $R_2$
For simplicity assume $R_A = R_C$; $R_{30} = R_{40}$. Then $$\frac{R_A - XR_B}{R_A - XR_D} = \frac{R_{30}\left(1 - \frac{\Delta t}{t_4}\right)}{R_{30}\left(1 - \frac{\Delta t}{t_3}\right)}$$

$$\frac{1 - X\frac{R_B}{R_A}}{1 - X\frac{R_D}{R_A}} = \frac{1 - \frac{\Delta t}{t_4}}{1 - \frac{\Delta t}{t_3}}$$

By the similarity of the expressions with regard to X and Δt, the values of $R_A$, $R_B$, $R_D$, $t_4$, and $t_3$ can be selected to provide a unique solution to the equation so that X corresponds to Δt as a measurable quantity.

Referring now to FIG. 6: If we write:

$$R_3 = R_{30}\left(\frac{1}{1 - nx}\right)$$

$$R_4 = R_{40}\left(\frac{1}{1 - x}\right)$$

Where
$R_3$ is thin element resistance
$R_{30}$ is thin element resistance when new
$R_4$ is thick element resistance
$R_{40}$ is thick element resistance when new
n is the ratio of thick to thin thickness x is proportional to the ratio of the decrease in thickness to the original thickness of the thin element
$R_1$ is a fixed resistor
$R_2$ is an equivalent resistance of $R_{2A}$, $R_{2B}$ and $R_{2C}$
$R_{2A}$ is a variable resistance = $R_{2AO}$ (1-2nx)
$R_{2B}$ is a fixed resistance in series with $R_{2A}$
$R_{2C}$ is a fixed resistance in parallel with series of $R_{2A}$ and $R_{2B}$
$R_{2AO}$ is maximum value of $R_{2A}$
Taking the ratio of $R_4/R_3$ we get $$\frac{R_4}{R_3} = \frac{R_{40}(1 - nx)}{R_{30}(1 - x)}$$

For bridge balance $$\frac{R_2}{R_1} = \frac{R_4}{R_3}$$

The ratio of $R_2/R_1$, can be derived mathematically to be:

$$R_2/R_1 = \frac{R_{2C}[R_{2B} + R_{2AO} - 2n \times R_{2AO}]}{R_1[R_{2B} + R_{2AO} + R_{2C} - 2n \times R_{2AO}]}$$

The expression can be rearranged to be similar to the expression for $R_4/R_3$ $$R_2/R_1 = \frac{R_{2C}(R_{2A} + R_{2B})\left(1 - \frac{2n \times R_{2AO}}{R_{2AO} + R_{2B}}\right)}{R_1(R_{2B} + R_{2AO} + R_{2C})\left(1 - \frac{2n \times R_{2AO}}{R_{2B} + R_{2AO} + R_{2C}}\right)}$$

letting $$\frac{R_{2C}(R_{2A} + R_{2B})}{R_1(R_{2B} + R_{2AO} + R_{2C})} = \frac{R_{40}}{R_{30}}$$

$$\frac{2R_{2AO}}{R_{2AO} + R_{2B}} = 1$$

$$\frac{2n R_{2AO}}{R_{2AO} + R_{2B} + R_{2C}} = 1$$

$$R_2/R_1 = \frac{R_{40}(1 - nx)}{R_{30}(1 - x)} = R_4/R_3$$

This is the equation for bridge balance.
The values of $R_1$, $R_{2AO}$, and $R_{2B}$ and $R_{2C}$ can be determined from the above equations for given values of n and $R_{40}/R_{30}$.
For example if $R_{40}/R_{30} = 1$:

$$R_{2AO} = R_{2B}$$

$$R_{2C} = R_{2AO}(n - 1)$$

$$R_1 = 2R_{2AO}\left(\frac{n - 1}{n}\right)$$

Letting $R_{2AO} = 1K$, n = 5:

$R_1 = 1.6K$ $R_{2AO} = 1K$ $R_{2B} = 1K$ $R_{2C} = 8K$

This result would provide a direct linear correspondence between the decrease in thickness of the corroding elements and the percentage of the variable resistance used in the circuit. The useable range of x is $0 < x < (1/2n)$ which gives the variable resistor from 0 to full value and thin element thickness which decreases to one half of the original thickness.

Various changes and modifications may be made to the structure of the present probe and measuring apparatus and the method of its use without departing from the spirit of the invention. It is intended that the present description be taken in illustration of the invention, and the appended claims define the scope thereof.

I claim:

1. A probe for monitoring the corrosion caused by a corrosive medium, said probe comprising a first corrodible electrical resistance element, a second corrodible electrical resistance element having a temperature-resistance characteristic similar to that of said first element, said elements being in the shape of rectangular prisms, each of said elements being positioned and adapted to have one lateral face exposed to said corrosive medium; the dimension of the transverse cross-section of said second element which is not exposed to the corrosive medium being greater than that of said first element; junction means connecting said element in series at one end thereof; separate terminal means connected to each said element at the end thereof opposite to the junction end; insulating means encasing said resistance elements except for said exposed lateral faces of said elements; and conductor means connected to said junction means and to said terminal means in a manner adapted to cause said first and second elements to function as adjacent but opposite resistance elements of a measurement bridge circuit and to enable connection of said probe to complementary elements of such measurement bridge circuit external to said probe.

2. The probe of claim 1 wherein said electrical resistance elements have substantially equal resistances and substantially equal thermal masses.

3. The probe of claim 2 wherein said electrical resistance elements have substantially equal lengths and cross-sectional areas.

4. The probe of claim 1 wherein said corrodible electrical resistance elements are made of the same material.

5. The probe of claim 1 comprising also support means adapted for flush mounting on pipelines or other structures.

6. Apparatus for measuring the corrosion caused by a corrosive medium comprising the probe of claim 1 in combination with other elements of a measurement bridge circuit, including two resistance arms in series, at least one of which is variable, a null detector connected between said junction means and the junction of said two resistance arms, and a current source connected between said terminal means connected to said first and second elements.

7. The apparatus of claim 6 wherein one of two said resistance arms is fixed and the other variable.

8. The apparatus of claim 6 wherein both said resistance arms are variable.

9. The apparatus of claim 6 where said current source comprises signal generating means.

10. A method for monitoring corrosion of a corrodible metal exposed to a corrosive medium comprising exposing only one lateral face of each of two adjacent, electrically opposite elements of a measurement bridge circuit to said medium, and determining the change in potential over a period of time between the junction of said two elements and the opposite junction of said bridge, while impressing a potential across the remaining two junctions of the bridge; said adjacent, electrically opposite bridge elements being in the shape of rectangular prisms, the dimension of the transverse cross-section of one of said elements which is not exposed to said corrosive medium being greater than that of the other element, and said elements having similar temperature-resistance characteristics.

11. The method of claim 10 wherein said adjacent, electrically opposite resistance elements of said measurement bridge circuit have substantially equal resistances and substantially equal thermal masses.

12. The method of claim 10 wherein said adjacent, electrically opposite resistance elements of said measurement bridge circuit have substantially equal lengths and cross-sectional areas.

13. The method of claim 10 wherein said adjacent, electrically opposite resistance elements of said measurement bridge circuit are made of the same material.

14. The method of claim 10 wherein one of the unexposed resistance arms of said measurement bridge circuit is fixed and the other variable.

15. The method of claim 10 wherein both of the unexposed resistance arms of said measurement bridge circuit are variable.

16. The method of claim 10 wherein said potential impressed across said remaining junctions of said measurement bridge circuit is supplied by a signal generator.

17. The apparatus of claim 7 wherein said variable resistance arm comprises a variable resistance and a first fixed resistance in series and a second fixed resistance in parallel with the series of said variable resistance and said first fixed resistance.

18. The apparatus of claim 8 wherein said variable resistance arms are ganged together.

19. The method of claim 14 wherein said variable resistance arm comprises a variable resistance and a first fixed resistance in series and a second fixed resistance in parallel with the series of said variable resistance and said first fixed resistance.

20. The method of claim 15 wherein said variable resistance arms are ganged together.

* * * * *